(12) United States Patent
Kojima et al.

(10) Patent No.: US 6,699,496 B1
(45) Date of Patent: Mar. 2, 2004

(54) ENZYME IN A DOSAGE FORM FOR ORAL USE IN MAMMALS, ENZYME-CONTAINING FOOD MATERIAL AND METHOD FOR ADMINISTERING THE ENZYME IN A DOSAGE FORM

(75) Inventors: Yuzo Kojima, Nagoya (JP); Hiroyasu Andoh, Nagoya (JP)

(73) Assignee: Amano Enzyme Inc., Nagoya (JP)

( * ) Notice: Subject to any disclaimer, the term of this patent is extended or adjusted under 35 U.S.C. 154(b) by 0 days.

(21) Appl. No.: 09/453,487

(22) Filed: Dec. 3, 1999

(30) Foreign Application Priority Data

Dec. 4, 1998 (JP) .......................... 10-361943
Nov. 24, 1999 (JP) .......................... 11-333076

(51) Int. Cl.$^7$ .............................. A61K 47/00
(52) U.S. Cl. ................... 424/439; 424/441; 424/442; 424/94.6
(58) Field of Search ................ 424/439, 441, 424/442, 94.6

(56) References Cited

U.S. PATENT DOCUMENTS

| 5,178,864 | A | * | 1/1993 | Lees et al. | ................... 424/94.1 |
| 5,273,753 | A | * | 12/1993 | Ishihara et al. | ............. 424/439 |
| 5,976,529 | A | * | 11/1999 | Navia et al. | ................ 424/96.6 |
| 6,042,823 | A | * | 3/2000 | Kimura et al. | ............. 424/94.5 |
| 6,051,220 | A | * | 4/2000 | Scharpe | .................... 424/94.2 |
| 6,083,538 | A | * | 7/2000 | Plijter et al. | ................... 426/20 |
| 6,183,739 | B1 | * | 2/2001 | Beudeker et al. | .......... 424/94.6 |
| 6,432,400 | B1 | * | 8/2002 | Chapus | ....................... 424/94.6 |

FOREIGN PATENT DOCUMENTS

| JP | 4-300825 | 10/1992 |

* cited by examiner

Primary Examiner—James H. Reamer
(74) Attorney, Agent, or Firm—Oblon, Spivak, McClelland, Maier & Neustadt, P.C.

(57) ABSTRACT

An enzyme in a dosage form for oral use in mammals is provided, wherein the enzyme has an activity of converting fat in a food material into 1,3-diglyceride and/or 1-monoglyceride. The enzyme has never been used conventionally for oral dosing to mammals. The enzyme in an oral dosage form can effectively decrease the body fat and/or internal fat in mammals in the course of general dietary life.

46 Claims, 1 Drawing Sheet

ENZYME IN A DOSAGE FORM FOR ORAL USE IN MAMMALS, ENZYME-CONTAINING FOOD MATERIAL AND METHOD FOR ADMINISTERING THE ENZYME IN A DOSAGE FORM

BACKGROUND OF THE INVENTION

1. Field of the Invention

The present invention relates to an enzyme in an oral dosage form, a food material(food stuff) containing the enzyme and a method for administering the enzyme in a dosage form; more specifically, the invention relates to an enzyme in a dosage form for oral use in mammals, a food material (food stuff) containing the enzyme and a method for administering the enzyme, wherein the enzyme is effective for decreasing the increased body fat and internal fat in mammals including humans, cattle, pet animals, when these increased fats are useless or harmful.

2. Description of the Related Art

The frequency of obesity in humans has been increasing due to excess calorie intake based on the recent change in their diets. The obesity functions as one cause for the induction of adult diseases. Because fat in particular readily accumulates in fat cells and is of high calorie, the individuals now pay significant attention to the fat intake from their diets. Alternatively, excessive accumulation of body fat in cattle such as cows and pigs is sometimes avoided from the respects of unpalatability as edible meat and nutritive control. Furthermore, the obesity of pet animals such as cats and dogs due to the ingestion of highly nutritious pet foods in recent years has been worrying their owners.

Recently, the physiological action and function of fat in mammals including humans, and the structure and the digestion and absorption of fat have been elucidated and reported. For example, JP-A-4-300825 remarks that 1,3-diglyceride (abbreviated to 1,3-DG hereinafter) suppresses more the increase in serum neutral fat after food ingestion and decreases more body fat, compared with triglyceride (abbreviated to TG hereinafter). In other words, it is suggested that the ingestion of 1,3-DG can effectively decrease body fat and internal fat (particularly, liver fat).

The reason is possibly as follows; 2-monoglyceride (abbreviated to 2-MG hereinafter) is primarily produced, with the action of the digestive juice in bodies, after TG ingestion. Then, 2-MG is readily converted to TG in the small intestines, which is then incorporated as TG (depot fat) in the liver and the like. Alternatively, 1-monoglyceride (hereinafter abbreviated to 1-MG) is produced with the action of the digestive juice, after 1,3-DG ingestion. However, the 1-MG is hardly converted into TG and is therefore hardly absorbed and stored as fat. In this case, additionally, fat incorporation in the liver is made principally via fatty acids from the portal vein. Accordingly, ketone bodies produced via β oxidation enhanced in the liver are excreted in urine. Thus, liver fat is decomposed and decreased.

With attention focused on what have been described above, conventionally, attempts have been made to procure the fat decreasing effect in humans or mammals, by a method comprising administering 1,3-DG extracted from natural materials or synthesized by chemical or enzymatic esterification (ester interchange reaction) and then contained in common edible oils and oil-containing foods, or comprising directly administering 1,3-DG in a dosage form.

However, the method comprising administering 1,3-DG separately from fat contained in food materials can hardly suppresses sufficiently 2-MG production per se derived from the fat contained in food materials, essentially, although the effects of 1,3-DG and 1-MG per se can be procured. Thus, the method can exert only limited effect on the decrease in body fat and internal fat.

Because 1-MG per se is so unstable that 1-MG can hardly be contained in such edible oils or oil-containing food materials, disadvantageously, the aforementioned method per se is hardly established in a practical sense.

SUMMARY OF THE INVENTION

It is an object of the invention to provide a means for effectively decreasing body fat and internal fat in mammals, by sufficiently utilizing the above findings about 1,3-DG and/or 1-MG. The present inventors have found that a certain enzyme conventionally never used for oral administration in mammals including humans can be used for the object. Thus, the invention has been achieved.

A first aspect of the invention relates to an enzyme in a dosage form for oral use in mammals, wherein the enzyme is capable of converting triglyceride in food materials into 1,3-diglyceride (1,3-DG) and/or 1-monoglyceride (1-MG).

According to the first aspect of the invention, the enzyme in an oral dosage form functions to convert the fat (TG) per se in the food materials into 1,3-DG and/or 1-MG which is hardly convertible to body fat or internal fat. Thus, the production of 2-MG from fat in food materials can sufficiently be suppressed. Consequently, the enzyme in an oral dosage form can satisfactorily decrease body fat and internal fat.

The inventors have not yet found any evidence that an enzyme having an activity of converting triglyceride into 1,3-DG and/or 1-MG has been utilized in a dosage form for oral use in mammals or any report telling the possibility. The function and advantage described above may be applied generally to mammals including humans, because mammals have common biological properties in terms of the structures of the digestive system including the liver and the physiological functions.

A second aspect of the invention relates to an enzyme in a dosage form for oral use in mammals, wherein the enzyme in the first aspect of the invention comprises at least one selected from the group consisting of lipase and esterase derived from the following microorganisms and biological organism 1 to 10.

1. *Geotrichum candidum*
2. *Candida rugosa*
3. *Candida lipolytica*
4. Pseudomonas sp.
5. *Aspergillus niger*
6. *Fhizopus oryzae*
7. Rhizopus sp.
8. *Mucor javanicus*
9. Porcine pancreas
10. *Penicillium camembertii*

The lipase or esterase derived from the 1 to 10 microorganisms and biological organism and the like is particularly effective as the enzyme in the oral dosage form. Additionally, because the enzyme per se has been well known conventionally and because of the oral dosage form, the lipase or esterase never exerts side effects harmful for mammals including humans.

A third aspect of the invention relates to a food material (food stuff) containing the enzyme according to the first aspect or the second aspect of the invention.

In accordance with the third aspect of the invention, the enzyme is contained in a food material. Thus, the resulting food material has the same advantage as those in the first and second aspects of the invention (without separately ingesting or administering the enzyme), and exhibits the same activity toward the fat contained in the resulting food material per se, or the fat in a fat-containing food material concurrently ingested with the resulting food material even when the food material only slightly contains fat.

A fourth aspect of the invention relates to a food material according to the third aspect of the invention, wherein the food material contains fat and the enzyme of 500 to 100,000 units per 100 g of fat [one unit of the enzyme generates 1 μmol fatty acid per one minute, as assayed at 37° C., pH 7 according to the fat digestion test described in the Section General Tests of the Japanese Pharmacopoeia; the definition applicable hereinafter].

In accordance with the fourth aspect of the invention, the enzyme is contained in an amount of 500 to 100,000 units per 100 g of fat in the enzyme-containing food material containing fat, whereby very excellent effect on the decrease in body fat or internal fat can be expected.

A fifth aspect of the invention relates to a method for administering the enzyme in an oral dosage form according to the first aspect or the second aspect of the invention, with a food material containing fat before, during or after meal.

The method for administering the enzyme in an oral dosage form according to the fifth aspect of the invention can bring function and advantage almost at the same levels as those in the first and second aspects of the invention.

The above and other advantages of the invention will become more apparent in the following description and the accompanying drawings.

DETAILED DESCRIPTION OF THE PREFERRED EMBODIMENTS

Figure 1:
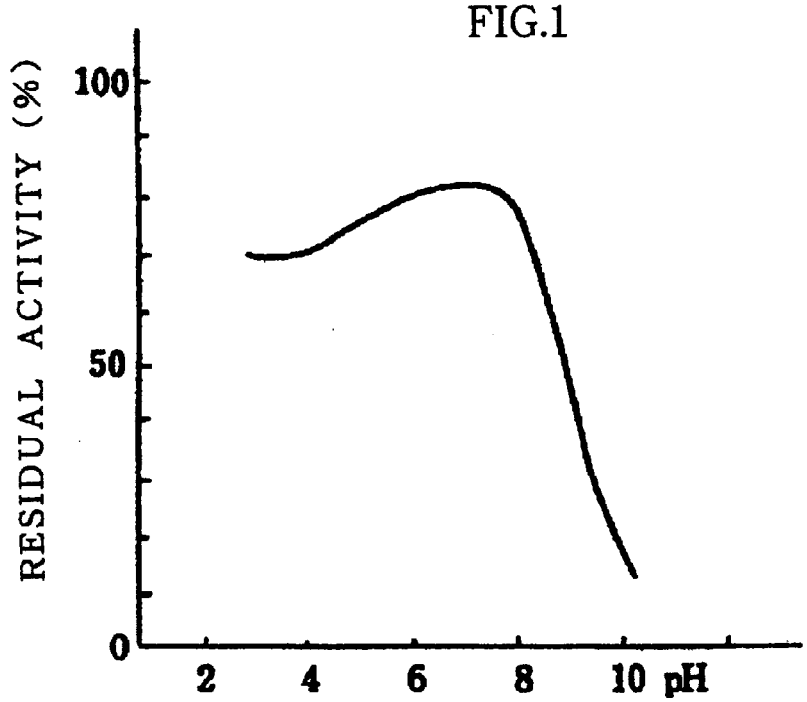
FIG. 1 is a graph depicting the stability of the lipase vs. pH in one example of the invention.

The first through fifth aspects of the invention will now be described in the following embodiments. Herein, the term "invention" collectively encompasses the first through fifth aspects of the invention.

Mammals

The scope of mammals is absolutely not limited in the invention. Mammals include for example humans, mammalian animals including cattle such as cows and pigs, pet animals such as dogs and cats, laboratory animals such as rats and monkeys, and various mammalian animals other than those belonging to the aforementioned categories.

Enzymes and Action

An enzyme capable of converting triglyceride into 1,3-DG and/or 1-MG is used as the enzyme in accordance with the invention. The enzyme belongs to the category generally called lipase (or esterase).

For the purpose of the production of 1,3-DG directly from TG, in accordance with the invention, use is particularly preferably made of nonspecific lipase capable of cleaving all the ester bonds at 1-, 2- and 3-positions in TG, which is derived from the microorganisms of the genera Geotrichum, Candida, and Penicillium; or lipase with the same action, which is derived from animals and plants. The content of lipase highly cleaving the ester bond at 2-position in TG is preferably increased, by fractionating isozymes contained in such enzymes.

Specific examples of such lipase include:
1. lipase from *Geotrichum candidum* (for example, Lipase GC AMANO under trade name, manufactured by Amano Pharmaceutical Co., Ltd.);
2. lipase from *Candida rugosa* (for example, Lipase AY AMANO under trade name, manufactured by Amano Pharmaceutical Co., Ltd.);
3. lipase from *Candida lipolytica* (for example, Lipase L AMANO under trade name, manufactured by Amano Pharmaceutical Co., Ltd.); and
4. lipase from Pseudomonas sp. (for example, Lipase P AMANO and lipase AK AMANO under trade names, manufactured by Amano Pharmaceutical Co., Ltd.).

In accordance with the invention, furthermore, 1,3-DG can be produced directly from TG with 1,3-specific lipase (such as microbial lipase derived from Aspergillus or Rhizopus, and lipase having the same action such as pancreas lipase and derived from animals or plants) which cleaves only the ester bond at 1-position or 3-position among the three ester bonds in TG , and by utilizing the spontaneous acyl migration to transfer the fatty acid at 2-position to 1-position, under specific conditions such as the increase of the dose of the 1,3-specific lipase or the lipase having the same action.

Specific examples of such lipase include:
5. lipase derived from *Aspergillus niger* (for example, Lipase AP AMANO under trade name, manufactured by Amano Pharmaceutical Co., Ltd.);
6. lipase derived from *Rhizopus oryzae* (for example, Lipase F AMANO under trade name, manufactured by Amano Pharmaceutical Co., Ltd.);
7. lipase derived from Rhizopus sp. (for example, Newlase AMANO under trade name, manufactured by Amano Pharmaceutical Co., Ltd.);
8. lipase derived from *Mucor javanicus* (for example, Lipase M AMANO under trade name, manufactured by Amano Pharmaceutical Co., Ltd.); and
9. lipase derived from porcine pancreas (for example, Pancreatin F AMANO under trade name, manufactured by Amano Pharmaceutical Co., Ltd.).

In accordance with the invention, lipase of the genus Penicillium as reported as diglyceride lipase in combination with one or more triglyceride lipase converts TG into 1-MG. Additionally, pancreas lipase can consequently produce 1-MG in mammalian bodies, even when only diglyceride lipase is used.

Specific examples of such lipase include:
10. lipase derived from *Penicillium camembertii* (for example, Lipase G AMANO under trade name, manufactured by Amano Pharmaceutical Co., Ltd.).

Enzyme Administering

In accordance with the invention, the various enzymes may satisfactorily be administered to mammals with a food material containing fat during meal, or before or after meal. These enzymes may be administered in oral dosage forms, separately from the food material or may be administered in the form of an enzyme-containing food material prepared by allowing a food material to preliminarily contain the enzyme. In short, a fat-containing food material and the enzyme should concurrently be present in the digestive tract of mammalian animals, so that the advantage of the invention can be realized.

As well known, a food material ingested in a mammalian animal is first digested with α-amylase secreted from the salivary glands, then with pepsin under acidic conditions owing to hydrochloric acid in the stomach, further with various enzymes secreted from pancreas in the intestines, and is finally absorbed as nutritious components through the intestinal wall.

The inventive enzyme coexists with substrates (food materials containing fat) in the stomach at the initial stage of digestion effectively, to produce 1,3-DG and 1-MG. Therefore, particularly preferred is the enzyme exerting its action sufficiently in the acidic circumstance of the stomach. In such a respect, the lipase derived from *Geotrichum candidum* and the like are specifically effective.

It can be expected that the various enzymes produce 1,3-DG not only in the stomach but also in the small intestines. Additionally, it can be expected that the enzymes convert 1,2-diglyceride (1,2-DG) produced by pancreatic lipase in the small intestines into 1-MG.

Enzyme in an Oral Dosage Form

The enzyme in a dosage form of the invention is used for oral dosing. The enzyme per se in powder or the like can be given or administered. If necessary, the enzyme is blended with other effective components while avoiding incompatibility or the enzyme is appropriately blended with various auxiliary agents, whereby an enzyme preparation with an appropriate composition and in a dosage form (powder, granule, liquid, solid, capsule, coated dosage form) can be obtained. Furthermore, the enzyme can be combined with an antacid, or can be used in combination with various drugs with an action on the digestive tract, such as $H_2$ blocker and proton pump inhibitor.

The enzyme in an oral dosage form may satisfactorily be ingested or administered at a dose capable of effectively producing 1,3-DG and/or 1-MG from fat-containing food materials in the mammalian digestive tract. The dose thereof to be administered or ingested is definitely determined with much difficulty, because the dose depends on the fat content in a food material, and the properties and purity of the enzyme used. One simple example is a single dose of 120 to 15,000 units.

Enzyme-containing Food Material

The inventive enzyme can preliminarily be contained in an appropriate food material. Any appropriate process is satisfactory for permitting a food material to contain the enzyme, such as a process of kneading the enzyme with ham, sausage, fish-kneaded product, bread or noodle dough, and solid feed, a process of adding the enzyme to a cooked food material by an appropriate means, and a process of mixing a powdery feed with the enzyme. Preferably, an enzyme with thermal stability may sometimes be selected, if necessary, for these processes.

Any type of food materials is satisfactorily used, with no specific limitation, but more reasonably, the enzyme is contained in a fat-containing food material. The amount of the enzyme contained in a fat-containing food material cannot be definitely determined because of the same reason as for the enzyme in an oral dosage form, but one example is 500 to 100,000 units per 100 g of fat in a food material, as in the fourth aspect of the invention.

Alternatively, the inventive enzyme may satisfactorily be contained in a food material slightly containing fat (for example, various food materials prepared from cereal materials). Because these food materials are often ingested concurrently with fat-containing food materials, the effect of the invention can effectively be realized.

By using coating or encapsulation techniques, the inventive enzyme preliminarily contained in an appropriate food material is preferably protected against low pH during food cooking and in the stomach after the ingestion of the food material.

EXAMPLES

Example 1

Lipase from *Geotrichum candidum* (for example, Lipase GC AMANO under trade name, manufactured by Amano Pharmaceutical Co., Ltd.) was fractionated on a Phenyl-Sepharose CL-4B column (manufactured by Pharmacia, Co.), to recover a lipase fraction highly hydrolyzing the ester bond at 2-position in TG.

Enzyme Stability Over pH

An enzyme solution (30 units/ml) of the lipase fraction was treated in buffers at various pHs at 37° C. for 30 minutes, to assay the residual activity; by designating the enzyme activity before the treatment as 100, the relative value of the residual activity is calculated as shown in FIG. 1. As apparent in FIG. 1, the enzyme sufficiently retained the activity at pH 4 to 8, indicating that the enzyme can be used satisfactorily for the reaction in the stomach.

Example 2

The lipase from *Geotrichum candidum* (for example, Lipase GC AMANO under trade name, manufactured by Amano Pharmaceutical Co., Ltd.) was used in the digestive tract model with emulsified olive oil as a substrate. As a result, the production of 1,3-DG was verified.

More specifically, a substrate solution was prepared by adding 0.067 mg/ml pepsin to a mixture of 6.86% emulsified olive oil, 0.1% stomach mucin, 150 mM $Na^+$, 1 mM $Ca^{2+}$ and 13 mM acetate buffer(pH 4); and by subsequently adjusting the resulting mixture to pH 4 with hydrochloric acid.

The substrate solution was retained at 37° C. in the stomach model, followed by addition of 500 units of lipase under mild agitation for the initiation of the reaction; up to 70 minutes after the initiation of the reaction, 0.1 N hydrochloric acid was added at a 15-min interval, so as to keep the model in the stomach circumstance, up to 120 minutes after the initiation of the reaction.

Figure 2:
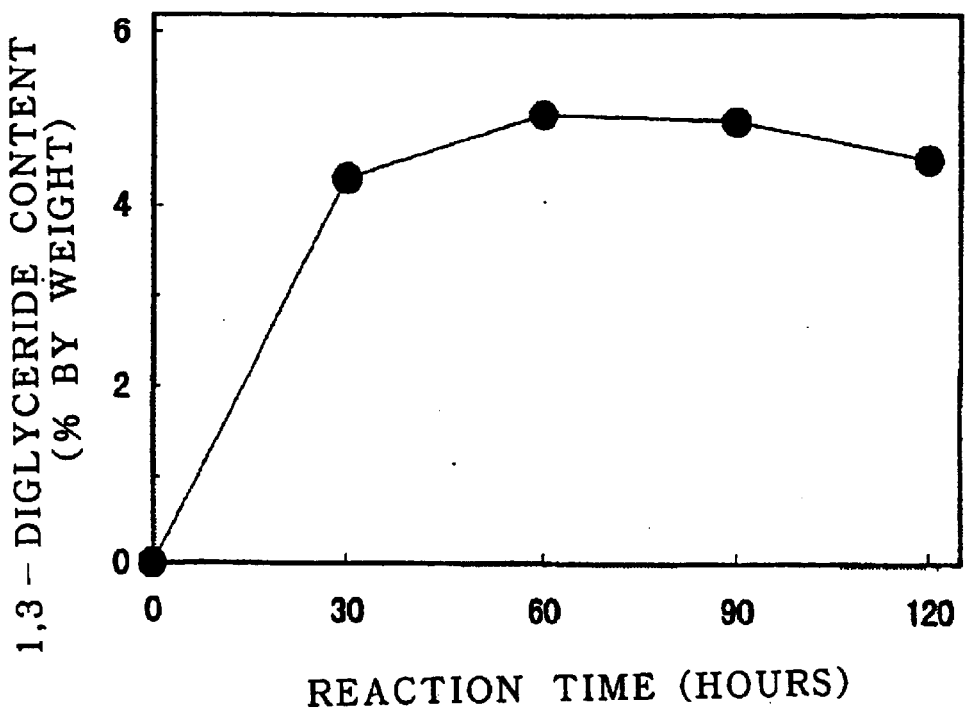
FIG. 2 is a graph of 1,3-DG generated by the lipase in another example of the invention.

The contents were sampled at a given interval during the reaction; hydrochloric acid was added to terminate the reaction; the oil was extracted in a chloroform/methanol (2/1) mixture solution, which was then assayed for 1,3-DG content by TLC-FID analyzer (manufactured by IATRON CO.). As shown in FIG. 2, 1,3-DG production in the stomach circumstance was verified.

Example 3

Using lipase from *Geotrichum candidum* (for example, Lipase GC AMANO under trade name, manufactured by Amano Pharmaceutical Co., Ltd.), the following animal experiments were carried out.

Experimental animals, namely male SD rats of 5 weeks of age, were preliminarily fed with a solid feed commercially available (CE-2 manufactured by CLEA JAPAN INC.) for 2 weeks; subsequently, the animals were divided into a control group of 5 animals and an experimental group of 5 animals. The rats were fed under the following conditions.

Temperature: 22±3° C.

Humidity: 55±10%

Artificial lightening: 12 hours daily (from 6 a.m. to 6 p.m.)

Breeding: individual rats kept in an SPF animal chamber.

Feed: 10 g of a powdery feed containing 10% rape seed oil was given three times/day, namely at 9 a.m., 2 p.m. and 6 p.m., daily.

The lipase was administered to the experimental group as follows. An aqueous 15 units/ml lipase solution was prepared and forcedly orally given at a single dose of 1 ml, three times, namely 10 a.m., 3 p.m. and 7 p.m., daily by using the stomach tube. The dosing was continued for 4 weeks. Instead of the aqueous lipase solution, water satisfying the Japanese Water Quality Standard of Water Supply was given to the control group in the same manner as described above. Furthermore, both of the groups were given water ad libitum.

On weeks 3 and 4, the body weight and body fat ratio of the animals in both of the groups were measured. Under anesthesia, body fat was measured by using a small animal body composition analysis system, Model SA-2, manufactured by EM-SCAN, CO. The results are shown as the mean (body weight in unit g) in each group in Table 1. The body fat ratio is represented as a ratio of a relative value of the 5 animals in the experimental group to the mean body fat value (designated 100) of the 5 animals in the control group on week 3 after the initiation of the dosing. The mark * in the table represents significant difference at the 5%-level of significance. As apparently shown in Table 1, the increase of body weight and body fat was observed in the control group, while the increase in body weight and body fat was likely to be suppressed in the experimental group.

TABLE 1

|  | Control group | | Experimental group | |
| --- | --- | --- | --- | --- |
|  | on week 3 | on week 4 | on week 3 | on week 4 |
| Body weight | 377 ± 16 | 395 ± 13 | 367 ± 10 | 374 ± 13 |
| Body fat ratio | 100 ± 4.4 | 106.4 ± 2.7* | 94.1 ± 3.4* | 100 ± 2.9 |

Example 4

Ten healthy human adults of slight to moderate obesity were randomly divided into a control group of 5 adults and an experimental group of 5 adults. The following clinical test was carried out.

Three tablets of the enzyme in an oral dosage form of the following composition as prepared and tableted in the conventional manner were given to the test subjects in the experimental group after each meal for 3 months. To the test subjects in the control group were given three tablets of the same composition except for the addition of lactose in place of lipase, after each meal for 3 months. Both of the groups could take any meal ad libitum, with no limitation to the contents of each meal, the number of meals, and the time of each meal.

| Lipase | 5 parts by weight. |
| --- | --- |
| Excipient (lactose) | 53 parts by weight. |
| Binder (crystal cellulose) | 40 parts by weight. |
| Fluidizing agent (light anhydrous silicic acid) | 1 part by weight. |
| Lubricant (magnesium stearate) | 1 part by weight. |

The body weight and body fat ratio of each test subject in both of the groups were measured for 3 days prior to the initiation of the test and for 3 days since the termination of the test; and the mean value for the two 3-day periods were calculated. Each test subject underwent an examination after awakening and before breakfast; the body fat ratio was measured by using a body fat meter of BIA type.

The results are shown as the mean value of each test group in Table 2. When the mean body weight and mean body fat ratio for 3 days prior to the initiation of the test were designated 100, the relative values of the mean body weight and mean body fat ratio for 3 days after the termination of the test are expressed in the table. The mark ** represents significant difference at the 1% level of significance. As apparently shown in Table 2, no significant change is observed in the body weight and body fat ratio in the control group, while a significant decrease is observed in the body fat ratio in the experimental group, with no significant change in the body weight in the experimental group.

TABLE 2

|  | Control group | Experimental group |
| --- | --- | --- |
| Body weight | 98.9 ± 2.3 | 98.1 ± 3.1 |
| Body fat ratio | 100.3 ± 3.6 | 92.3 ± 3.2** |

In the experimental group with the ingestion of the enzyme in an oral dosage form of the invention after meal, 1,3-DG is produced in the digestive tract from TG in the oil and fat contained in edible oil and food, whereby the body fat ratio is significantly decreased.

Example 5

For the same measurement, the same animal experiments as in Example 3 were carried out by dosing lipase derived from *Penicillium camembertii* (Lipase G AMANO under trade name, manufactured by Amano Pharmaceutical Co., Ltd.) at a dose of 15 units/ml. The results are shown in Table 3; like Example 3, the increase in body fat was apparently suppressed in the experimental group, compared with the control group.

TABLE 3

|  | Control group | | Experimental group | |
| --- | --- | --- | --- | --- |
|  | on week 3 | on week 4 | on week 3 | on week 4 |
| Body weight | 369 ± 13 | 388 ± 16 | 362 ± 11 | 381 ± 15 |
| Body fat ratio | 100 ± 3.2 | 104.3 ± 4.1* | 96.1 ± 2.0* | 101 ± 4.8 |

Example 6

The same animal experiments as in Example 3 were carried out, except that forced oral dosing of the aqueous lipase solution or water using the stomach tube was not effected to the experimental group nor the control group, and that instead an enzyme-containing food material prepared by preliminarily blending 15 units of lipase derived from Geotrichum candidum (Lipase GC AMANO under trade name, manufactured by Amano Pharmaceutical Co., Ltd.) per 10 g of feed was given as a feed for the experimental group. The same measurement was carried out.

The results are shown below in Table 4. Like Example 3, the increase in body fat was apparently suppressed in the experimental group, compared with the control group.

TABLE 4

|  | Control group | | Experimental group | |
| --- | --- | --- | --- | --- |
|  | on week 3 | on week 4 | on week 3 | on week 4 |
| Body weight | 362 ± 14 | 389 ± 11 | 358 ± 11 | 380 ± 15 |
| Body fat ratio | 100 ± 3.9 | 104.7 ± 3.3 | 92.5 ± 3.3* | 96.7 ± 3.7 |

While the preferred embodiments have been described, variations thereto will occur to those skilled in the art within the scope of the present inventive concepts which are delineated by the following claims.

What is claimed is:

1. An enzyme in a dosage form for oral use for effectively decreasing body fat and internal fat in mammals, wherein the enzyme is capable of converting triglyceride in a food material into 1,3-diglyceride (1,3-DG) and/or 1-monoglyceride (1-MG), wherein the enzyme is blended with one or more drug(s) with an action on the digestive tract selected from the group consisting of an antacid, an $H_2$ blocker and a proton pump inhibitor.

2. An enzyme-containing food material containing
an enzyme capable of converting triglyceride in a food material into 1,3 diglyceride (1,3-DG) and/or 1-monoglyceride (1-MG),
wherein fat is contained in the food material and wherein the enzyme is contained at 500 to 100,000 units per 100 g of fat in the food material.

3. A method for administering an enzyme in a dosage form for oral use in mammals, comprising
administering an enzyme capable of converting triglyceride in a food material into 1,3 diglyceride (1,3-DG) and/or 1-monoglyceride (1-MG) with a fat containing food material,
wherein the enzyme in a dosage form is administered at a single dose of 120 to 15,000 units.

4. A composition comprising an enzyme, which converts a triglyceride into 1,3-diglyceride (1,3-DG) and/or 1-monoglyceride (1-MG), in an amount effective to decrease body fat or internal fat in a mammal and in a form suitable for oral administration to a mammal.

5. The composition of claim 4, wherein said enzyme hydrolyzes an ester bond at the second carbon of a triglyceride.

6. The composition of claim 4, wherein said enzyme is from *Geotrichum candidum*.

7. The composition of claim 4, wherein said enzyme is obtained by fractionation of a composition comprising one or more *Geotrichum candidum* lipase(s).

8. The composition of claim 4 that comprises an isolated *Geotrichum candidum* isozyme that cleaves an ester bond at the 2-position of a triglyceride.

9. The composition of claim 4, further comprising one or more auxiliary agent(s).

10. The composition of claim 4 in the form of a powder.

11. The composition of claim 4 in the form of a granule.

12. The composition of claim 4 in the form of a solid, capsule or a coated dosage form.

13. The composition of claim 4 in liquid form.

14. A composition comprising
an enzyme that converts a triglyceride into 1,3-diglyceride (1,3-DG) and/or 1-monoglyceride (1-MG) and
one or more drug(s) with an action on the digestive tract selected from the group consisting of an antacid, an $H_2$ blocker and a proton pump inhibitor,
wherein said composition is in a form suitable for oral administration and said enzyme is present in an amount effective to decrease body fat or internal fat in a mammal.

15. The composition of claim 14, wherein said enzyme hydrolyzes an ester bond at the second carbon of a triglyceride.

16. The composition of claim 14, wherein said enzyme is from *Geotrichum candidum*.

17. The composition of claim 14, wherein said enzyme is obtained by fractionation of a composition comprising one or more *Geotrichum candidum* lipase(s).

18. The composition of claim 14, which comprises an isolated *Geotrichum candidum* isozyme that cleaves an ester bond at the 2-position of a triglyceride.

19. The composition of claim 14, comprising an antacid.

20. The composition of claim 14, comprising an $H_2$ blocker.

21. The composition of claim 14, comprising a proton pump inhibitor.

22. A food supplemented with an enzyme, which coverts a triglyceride in a food material into 1,3-diglyceride (1,3-DG) and/or 1-monoglyceride (1-MG).

23. The food of claim 22, wherein said enzyme hydrolyzes an ester bond at the second carbon of a triglyceride.

24. The food of claim 22, wherein said enzyme is from *Geotrichum candidum*.

25. The food of claim 22, wherein said enzyme is obtained by fractionation of a composition comprising one or more *Geotrichum candidum* lipase(s).

26. The food of claim 22, which comprises an isolated *Geotrichum candidum* isozyme that cleaves an ester bond at the 2-position of a triglyceride.

27. The food of claim 22 wherein said food comprises fat.

28. The food of claim 22 that comprises from 500 to 100,000 units of said enzyme per 100 grams of fat.

29. The food of claim 22 that is fat free.

30. The food of claim 22 that is a cereal, bread or noodle dough.

31. The food of claim 22 that is ham, sausage, fish cake, or a fish-kneaded product.

32. The food of claim 22 that is a solid or powdery feed.

33. A method for decreasing body fat or internal fat comprising administering to a subject in need thereof an enzyme that converts a triglyceride into 1,3-diglyceride (1,3-DG) and/or 1-monoglyceride (1-MG).

34. The method of claim 33 wherein said enzyme hydrolyzes an ester bond at the second carbon of a triglyceride.

35. The method of claim 33, wherein a single dosage comprising 120 to 15,000 units of said enzyme are administered.

36. The method of claim 33, wherein said enzyme is from *Geotrichum candidum*.

37. The method of claim 33, wherein said enzyme is obtained by fractionation of a composition comprising one or more *Geotrichum candidum* lipase(s).

38. The method of claim 33, wherein said enzyme is an isolated *Geotrichum candidum* isozyme that cleaves an ester bond at the 2-position of a triglyceride.

39. The method of claim 33, wherein said enzyme is administered before or after a meal.

40. The method of claim 33, that comprises administering said enzyme to a human.

41. The method of claim 33, that comprises administering said enzyme to cattle or a pet animal.

42. A method for suppressing the formation of 2-monoglyceride (2-MG) from fat comprising
administering to a subject in need thereof an enzyme that coverts a triglyceride into 1,3-diglyceride (1,3-DG) and/or 1-monoglyceride (1-MG).

43. The method of claim 42, wherein said enzyme hydrolyzes an ester bond at the second carbon of a triglyceride.

44. The method of claim 42, wherein said enzyme is from *Geotrichum candidum*.

45. The method of claim 42, wherein said enzyme is obtained by fractionation of a composition comprising one or more *Geotrichum candidum* lipase(s).

46. The method of claim 42, wherein said enzyme is an isolated *Geotrichum candidum* isozyme that cleaves an ester bond at the 2-position of a triglyceride.

* * * * *